United States Patent [19]
Hammes et al.

[11] Patent Number: 6,093,745
[45] Date of Patent: Jul. 25, 2000

[54] METHODS AND COMPOSITION FOR TREATING SKIN PROLIFERATIVE DISEASES

[75] Inventors: Hans-Peter Hammes, Linden, Germany; Michael Brownlee, New York, N.Y.

[73] Assignee: PsoRx, L.L.C., Palo Alto, Calif.

[21] Appl. No.: 08/978,035

[22] Filed: Nov. 25, 1997

[51] Int. Cl.[7] .................................................. A61K 31/155
[52] U.S. Cl. .............................................................. 514/634
[58] Field of Search ............................................. 514/634

[56] References Cited

U.S. PATENT DOCUMENTS

| | | |
|---|---|---|
| 4,006,249 | 2/1977 | Porter et al. . |
| 4,201,788 | 5/1980 | Voorhees et al. . |
| 4,618,344 | 10/1986 | Wells .......................................... 8/161 |
| 5,449,688 | 9/1995 | Wahl et al. . |
| 5,501,849 | 3/1996 | Lee . |
| 5,534,551 | 7/1996 | Page et al. .............................. 514/634 |
| 5,607,679 | 3/1997 | Rhodes . |

FOREIGN PATENT DOCUMENTS

WO 96/12483  5/1996  WIPO .

OTHER PUBLICATIONS

Erdman et al., (1989) *Gastroenterology*, 96:1533–1538.
Heck et al., (1992) *Journal of Biological Chemistry* 267:21277–21280.
Misko et al. (1993) *European Journal of Pharmacology*, 233:119–125.
Kolb–Bachofen et al. (1994) *Lancet*, 344:139.
Morhenn, Vera B. (1997) *Immunology Today*, 18:433–436.
Rokkas et al., (1990) *Digestion* 46:447–457.
Saeki et al. (1975) *The Journal of Pharmacology and experimental Therapeutics*, 193:910–917.
Sirsjö et al. (1996) *British Journal of Dermatology*, 134:643–648.
Sugiyama et al., (1993) *Toxicology Letters*, 69:273–278.

*Primary Examiner*—James H. Reamer

[57] ABSTRACT

Methods and a compositions are provided for treating a skin proliferation disease such as psoriasis to inhibit the proliferation of epidermal cells, particularly keratinocytes and to reduce the symptoms of erythematous scales associated with the disease. The method comprises administering to a mammalian host with a skin proliferation disease a composition comprising an effective amount of an aminoguanidine composition, generally in a pharmaceutically acceptable carrier. The invention also provides a composition comprising an aminoguanidine composition which can be formulated in a pharmaceutically acceptable carrier, in a topical application form or for oral administration. The composition finds use in alleviating symptoms associated with the disease, such as reducing size, thickness or scales of a psoriatic lesion, reducing erthema, decreasing itching and decreasing induration.

6 Claims, 3 Drawing Sheets

(3 of 3 Drawing Sheet(s) Filed in Color)

METHODS AND COMPOSITION FOR TREATING SKIN PROLIFERATIVE DISEASES

INTRODUCTION

1. Technical Field

This invention relates to a method of treating non-malignant proliferative diseases of the skin. This invention is exemplified by the use of a composition comprising aminoguanidine to treat psoriasis.

2. Background

Proliferative skin diseases are widespread throughout the world and afflict millions of humans and their domesticated animals. Proliferative skin diseases are characterized by keratinocyte cell proliferation, or division, and may also be associated with incomplete epidermal differentiation. Keratinocyte hyperproliferation has been seen in the absence of inflammatory infiltrate in an experimental model of psoriasis, but inflammation is not seen without keratinocyte hyperproliferation and abnormal differentiation (Carroll et al *Cell* 83:957 (1995)).

Psoriasis is the most serious of the proliferative skin diseases with which this invention is concerned. The incidence of psoriasis in the United States is about 2% of the population.

About 3% of whites and 1% of blacks are affected. Occurrence is extremely low in Native Americans. Psoriasis affects both sexes equally. It occurs in about 2.5% of HIV-infected patients. Abortive forms of psoriasis share many features with seborrheic dermatitis, a disease affecting at least 2 to 5 percent of the population; clinically and histologically the lesions of chronic seborrheic dermatitis are often difficult to distinguish from those of psoriasis.

Psoriasis is a genetically determined disease of the skin characterized by two biological hallmarks. First, there is a profound epidermal hyperproliferation related to accelerated and incomplete differentiation. Second, there is a marked inflammation of both epidermis and dermis with an increased recruitment of T lymphocytes, and in some cases, formation of neutrophil microabcesses. Many pathologic features of psoriasis can be attributed to alterations in the growth and maturation of epidermal keratinocytes, with increased proliferation of epidermal cells, occurring within 0.2 mm of the skin's surface. Traditional investigations into the pathogenesis of psoriasis have focused on the increased proliferation and hyperplasia of the epidermis. In normal skin, the time for a cell to move from the basal layer through the granular layer is 4 to 5 weeks. In psoriatic lesions, the time is decreased sevenfold to tenfold because of a shortened cell cycle time, an increase in the absolute number of cells capable of proliferating, and an increased proportion of cells that are actually dividing. The hyperproliferative phenomenon is also expressed, although to a substantially smaller degree, in the clinically uninvolved skin of psoriatic patients.

A common form of psoriasis, psoriasis vulgaris, is characterized by well-demarcated erythematous plaques covered by thick, silvery scales. A characteristic finding is the isomorphic response (Koebner phenomenon), in which new psoriatic lesions arise at sites of cutaneous trauma. Lesions are often localized to the extensor surfaces of the extremities, and the nails and scalp are also commonly involved. Much less common forms include guttate psoriasis, a form of the disease that often erupts following streptococcal pharyngitis, and pustular psoriasis, which is characterized by numerous sterile pustules, often 2 to 5 mm in diameter, on the palms and soles or distributed over the body.

Therapeutic efforts in psoriasis are aimed at decreasing the proliferative rate of the epidermis, either by direct action on cell division or indirectly by reducing the immunological response with agents that reduce the inflammatory response or vascular permeability (Guzzo, *C. Derm. Clinics* 15:59 (1997)). For patients with localized, limited psoriasis, administration of topical corticosteroids is the most convenient outpatient therapy. Rapid improvement may be seen with this approach, but the beneficial short-term efficacy is limited and chronic topical corticosteroid treatment is not advisable. Side effects from chronic topical corticosteroid therapy can include atrophy of the skin, development of tolerance to the agent used (tachyphylaxis), and serious exacerbation of the disease after discontinuation. Pituitary-adrenal suppression is a potential and serious complication of potent topical corticosteroid therapy, particularly when the agent covers a large portion of the body surface and is used under occlusive dressings. Despite these potential drawbacks, topical corticosteroid therapy, in combination with emollients or used alone, remains the most commonly prescribed treatment for psoriasis.

Other treatments used for localized disease include topical application of calcipotriene, coal tar preparations, or tazarotene. Calcipotriene is a vitamin D3 derivative that may be applied topically twice daily to improve plaque-type psoriasis. At recommended dosages, calcium metabolism appears to be minimally affected, although hypercalcemia has been seen in patients using excessive amounts of the topical ointment. The safety and efficacy of this treatment have not been established beyond 8 weeks of therapy. Topical coal tar preparations have been effective when used alone to clear psoriatic plaques by inhibiting mitotic activity in the epidermis; however, the unpleasant odor of the preparations and the propensity to stain fabrics reduce the acceptance of these preparations by patients. Hospitalization may be required for patients with more extensive disease, who are treated with topical coal tar preparations followed by irradiation with B-spectrum ultraviolet light (290 to 320 nm). This regimen, known as Goeckerman's regimen, can be modified to include the use of topical steroids. Intensive tar and ultraviolet B exposure can lead to development of skin cancer, especially in people with fair skin. It has been reported that in 50% to 70% of patients with mild to moderate psoriasis treated with either 0.05% or 0.1% concentration of tazarotene (a retinoid), produced an improvement or a complete clearing of lesions. However, irritation, burning, stinging, pruritus and erythema can occur at the site of application, especially with the 0.1% gel. After four months of use, some patients reported aggravation of the disease and an increased erthema response to sunlight (G D Weinstein *J Am Acad Dermatol* 37:S33 (1997)).

For patients with extensive disease, systemic antimitotic agents such as methotrexate are used. Methotrexate usually is administered on an intermittent basis and should not be given more frequently than once weekly. Patients receiving it should be monitored for hematologic and liver toxicity; because methotrexate-induced cirrhosis is a risk, especially after a cumulative dose of 1.5 g has been reached, liver biopsy may be indicated.

Extensive psoriasis can also be treated with photochemotherapy. In this regimen, oral 8-methoxypsoralen produces photosensitization, which is followed by exposure to ultraviolet A (PUVA, 320 nm). Like Goeckerman's regimen (supra), this therapy inhibits mitotic activity in the epidermis, and it produces remissions in up to 80% of patients with plaque-type psoriasis. It seems to be less useful in patients with pustular psoriasis. Major complications of PUVA therapy are acute sunburn and the risk of corneal damage. Eyes must be protected for up to 24 hours after ingestion of psoralen. PUVA therapy may cause retinal damage in aphakic persons and is therefore contraindicated in these patients. Also, skin cancer develops in 2% of patients on PUVA. Fair-skinned people with long histories of exposure to ultraviolet irradiation are at the highest risk of developing skin cancer.

The retinoids, particularly etretinate, either alone or in combination with PUVA, are also an effective treatment for psoriasis. Etretinate is especially useful in the exfoliative and pustular varieties of psoriasis. However, several major potential complications must be monitored in patients placed on retinoids. As a class, the retinoids are potent teratogens and should not be given to women of childbearing age who are not using adequate contraception. Etretinate, like other retinoids, can produce elevations in cholesterol and triglyceride levels, therefore dietary regulation may be necessary. In addition, because etretinate can induce hepatotoxicity, liver function tests should be performed before and at regular intervals during use of the drug. Because the half-life of etretinate is about 6 months, if hepatotoxicity develops, close monitoring is required. For HIV-positive patients with severe psoriasis, etretinate may be the best therapeutic strategy.

Cyclosporin A has been shown to be an effective treatment of psoriasis. The results of clinical trials using low-dose (3 to 7 mg/kg) cyclosporin A are impressive, because the time required to achieve complete remission ranges from 1 to 4 weeks. However, the use of cyclosporin A should be reserved for patients with recalcitrant, debilitating psoriasis when the benefits outweigh the potential risk of complications. The major adverse effects of cyclosporin A with short-term, low-dose usage include potential renal dysfunction and hypertension. The renal toxicity is usually reversible if low doses were used upon discontinuing therapy; however, irreversible renal damage may occur with a prolonged treatment course. Patients who have previously received extensive phototherapy, particularly PUVA, must be monitored for the development of invasive squamous cell carcinomas of the skin. F506 (tacrolimus), a functionally similar drug to cyclosporin A, is also effective in treating severe recalcitrant psoriasis, but has similar side effects by cyclosporin A.

Considering the complications and side effects attendant to the use of different drugs and photochemotherapy currently used in treating a skin proliferative disease such as psoriasis, there is a need for a new method and a new composition to inhibit keratinocyte proliferation to alleviate the symptoms of skin proliferation diseases. The new composition ideally is well tolerated by patients, is easy to manufacture and relatively inexpensive. The new method is ideally easy to use with patients, it reduces the symptoms of skin proliferation disease in a short period of time, and it presents no significant health complications and/or risks.

Relevant Literature

U.S. Pat. No. 4,006,249 is directed to a process for ameliorating the clinical manifestation of psoriasis in humans by systemic administration of 2,6-dihalobenzylideneaminoguanidines, aromatic derivatives of aminoguanidine.

U.S. Pat. No. 5,607,679 is directed to a method of treatment of a skin disease caused by or associated with hyperproliferation of keratinocytes or hyperkerotosis by administering a lectin which is capable of binding a sialylated TF antigen.

U.S. Pat. No. 4,201,788 is directed to a process for treating non-malignant proliferative skin diseases by administering to the afflicted human or other animal a composition containing 1,1' methylethanediylidinedinitrilo-bis-(3-aminoguanidine).

U.S. Pat. No. 5,449,688 is directed to a method for treating a mammal having a chronic inflammatory condition selected from the group consisting of arthritis, periodontitis gingivitis, granulomas, and fibrosis, by administering an effective amount of aminoguanidine.

WO96/12483 describes a method of inhibiting nitric oxide production in a warm blooded mammal afflicted with the physiological conditions manifested in an acute or chronic inflammatory disease or condition, which comprises administering to said mammal a nitric oxide inhibitory effective amount of inhibitory compound of aminoguanidine. However, the literature relating to the relationship between nitric oxide production and cell proliferation is taught with apparently contradictory reports. Inducible nitric oxide synthase mRNA and protein are increased in epidermal keratinocytes of psoriatic lesions (Kolb-Bachofen et al *J. Exp. Med.* 344:139 (1994); Sirsjo et al Br. *J. Derm.* 134:643 (1996)). It has been suggested that overproduction of nitric oxide may cause the characteristic abnormalities of psoriasis (Morhenn, V. B. *Immunology Today* 18:433 (1997)). Conversely, nitric oxide has been shown to inhibit keratinocyte proliferation (Heck et al (1992) *J. Biol. Chem.* 267:21277; Arock et al *J. Invest. Derm.* 103:422 (1994)), in a manner analogous to its inhibition of vascular smooth muscle cell proliferation (Garg, et al *J. Clin. Invest.* 83:1774 (1989); Nakaki et al *Eur J Pharmacol* 189:347 (1990)), neuronal proliferation (Peunova et al *Nature* 375:68 (1995)), and hepatoma cell proliferation (Kurose et al *Gastroenterology* 111:1058 (1996)). In human keratinocytes, nitric oxide induced by inflammatory mediators inhibits keratinocyte growth, and this growth-inhibitory effect is reversed by NMMA, a specific inhibitor of nitric oxide synthetase (Heck et al *J. Biol. Chem.* 267:21277 (1992)). In animals, nitric oxide enhances the suppresser function of macrophages, (Albina et al *J Immunol.* 147:144 (1991); Mills, C. D. *J. Immunol.* 146:2719 (1991); Balligand et al *J. Clin. Invest.* 91:2314 (1993)), inhibits T-cell proliferation (Hoffman et al *J. Immunol.* 145:2220 (1990); Fu et al *J. Immunol.* 148:2217 (1992); Denham et al *Clin. Exp. Immunol.* 87:157 (1992)), and inhibits the secretion of IL-2 and IFNγ by $TH_1$ cells (Taylor-Robinson et al *Eur J Immunol.* 24:980 (1994); Taylor-Robinson al *Immunol. and Cell Biol.* 75:167 (1997)).

Aminoguanidine has been reported to inhibit the inducible form of nitric oxide synthetase (Misko et al *Eur. J. Pharmacol.* 233:119 (1993)). Apparently contradictory results have been reported regarding the effects of aminoguanidine on proliferation of various cell types. Aminoguanidine enhanced ileal mucosal proliferation in treated rats after ileal resection (Erdman et al *Gastroenterology* 96:1533 (1989); Rokkas et al *Digestion* 46 Suppl 2:447 (1990)), but diminished induced granulation tissue proliferation occurring in skin of treated rats (Saeki et al *J of Pharmacol and Experimental Therapeutics* 193:910 (1975)). In cell culture, aminoguanidine has been reported to inhibit proliferation of rat liver and human cervical cancer (HeLa-53) cells (Sugiyam et al *Toxicol. Letters* 69:273 (1993)).

U.S. Pat. No. 5,501,849 discloses an emollient composition for use in a psoriasis treatment in which abnormal skin is exposed to an incident therapeutic radiation, wherein said active agent is trimethylpsoralen, 8-methoxy psoralen or urocanic acid. Stjernborg et al *Biochem. Par.* 45:1174–1176 (1993)) report that aminoguanidine stabilized and increased S-adenosylmethionine decarboxylase protein and enzyme activity. Svensson et al *Biochem. J.* 322:297–302 (1997)) report aminoguanidine inhibits S-adenosylmethionine decarboxylase.

SUMMARY OF THE INVENTION

This invention relates to a method and a composition for alleviating at least one symptom of a skin disease in a mammalian host caused by or associated with hyperproliferation of keratinocytes as compared with a host who has no treatment. The symptoms which are alleviated include the inappropriate proliferation and hyperplasia of epidermal cells, and the symptoms relating to erythematous plaques, such as the thickness and size of lesion, scaling and pruritis (itching). The method includes the step of administering to a patient afflicted with a skin proliferation disease a composition containing an effective amount of aminoguanidine in a pharmaceutically acceptable carrier to alleviate at least one symptom. The invention also provides a composition comprising aminoguanidine or a salt thereof formulated in a pharmaceutically acceptable carrier, in a form for topical application. The composition finds use in the treatment of skin proliferation diseases such as psoriasis, to inhibit proliferation of epidermal cells and to alleviate lesions and other symptoms associated with the disease.

DESCRIPTION OF THE FIGURES

The file of this patent contains at least one drawing executed in color. Copies of this patent with color drawing (s) will be provided by the Patent an Trademark Office upon request and payment of the necessary fee.

DETAILED DESCRIPTION OF THE PREFERRED EMBODIMENTS

Figure 1A:
FIGS. 1A and 1B are images of a patient inflicted with a psoriasis lesion on one side of his head treated with vehicle alone (FIG. 1A) and then with aminoguanidine in the vehicle (FIG. 1B).

This invention relates to a method and a composition for treating a skin proliferation disease which is caused by or associated with hyperproliferation of keratinocytes. A mammalian host subject to hyperproliferative skin disorders due to hypeproliferation of keratinocytes is treated with a formulation comprising aminoguanidine or a salt thereof generally for a period of 3 days to 4 weeks, beginning at the first observable symptoms of onset of a hyperproliferative episode and continuing until the symptoms of the skin disorder improves or disappears. The formulation according to the invention may be administered for therapy by any suitable routes, including topical and oral routes. It will be appreciated that the preferred route will vary with the condition and age of the patient, and how long-lasting the treatment is. A preferred route of administering an aminoguanidine formulation is by topically applying the formulation at the site of the disease for exertion of local action. The treatment inhibits the proliferation and hyperplasia of epidermal cells and alleviates associated symptoms, such as decreasing the size and thickness of a lesion and reducing scaling and pruritis.

The subject invention does not present significant health complications and/or risk, is easy to use with patients, and is well tolerated. It thus has advantages over current treatment methods which have complications and side effects such as atrophy of skin, tachyphylaxis, hypercalcemia, liver toxicity, skin cancer, renal toxicity and hypertension. The symptoms of the skin disorder are alleviated in a short time period. For a patient afflicted with an acute or a severe skin proliferation disease, the method of this invention can be combined with other conventional treatments such as a topical treatment with corticosteroids, retinoids, calcipotrene, coal tar preparations, a systemic treatment with methotrexate, retinoids, cyclosporin A and photochemotherapy. The combined treatment with the subject formulation makes the treatment more effective, and/or allows lower, less toxic doses of other agents to be used, thus decreasing the side effects of the currently used treatment modalities. Intermittent pulse therapy such as treatment for several days or weeks with topical steroids alternating with treatment with an aminoguanidine composition may prevent development of tachyphylaxis associated with topical steroids.

The compositions employed in this invention comprise compounds that bear a guanidinium group and include aminoguanidine and its structurally related compounds such as guanidine aminovaleric acid (arginine) derivatives, for example, N-amino-L-arginine, N-nitro-arginine, N-monomethyl-L-arginine, N-nitro-L-arginine methyl ester and N-amino-L-arginine. N-monomethyl-L-arginine is comercially available from Calbiochem (La Jolla, Calif.). Aminoguanidine, N-amino-L-arginine, N-nitro-arginine, N-nitro-L-arginine methyl ester are commercially available from Sigma Chemical Co. (St. Louis, Mo.). N-amino-L-arginine is not commercially available; however, it may be synthesized by the methods described in *Biochem, Biophys. Res. Comm.*, 168, 458 (1990) or *Biochem, Biophys. Res. Comm.* 168:458 (1990). Aminoguanidine is also available in a pharmaceutical grade from Fairmount Chemical Co., Inc. (Newark, N.J.), Hummel Croton, Inc. (South Plainfield, N.J.), Nippon Carbide Industries Co., Inc. (Tokyo, Japan), Organosulf Chemical Fabrik GmbH (Germany) and Toyokosei Kogyo Co., Ltd. (Isaka, Japan). Generally, the purity of aminoguanidine for use in a pharmaceutical application is >98%. A preferred compound in this invention is aminoguanidine or an acidic salt thereof, for example a bicarbonate, a hemisulfate and a hydrochloride salt.

While it is possible for the aminoguanidine composition to be administered alone, it is preferable to formulate the active ingredient as a pharmaceutical formulation. By "aminoguanidine composition" is intended a composition comprising aminoguanidine, or its structurally related compounds such as arginine derivatives, or an acidic salt thereof. The pharmaceutical formulations of the present invention comprise an effective amount of an aminoguanidine composition, together with one or more pharmaceutically-acceptable carriers. An "effective amount" of an aminoguanidine composition is the amount sufficient to alleviate at least one symptom of a skin proliferation disease. The effective amount will vary depending upon several factors, including the age and weight of the patient, how advanced the disease state is, the general health of the patient, the severity of the symptoms, and whether the aminoguanidine formulation is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

Aminoguanidine formulations include those suitable for topical and oral administration, with topical formulations being preferred. The topical formulations include those pharmaceutical forms in which the composition is applied externally by direct contact with the skin surface to be treated. A conventional pharmaceutical form for topical application includes a soak, an ointment, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. As an example, an acute skin proliferation disease generally is treated with aqueous drying preparations, whereas chronic skin proliferation disease is treated with hydrating preparations. Soaks are the easiest method of drying acute moist eruptions. Lotions (powder in water suspension) and solutions (medications dissolved in a solvent) are ideal for hairy and intertriginous areas. Ointments or water-in-oil emulsions, are the most effective hydrating agents, appropriate for dry scaly eruptions, but are greasy and depending upon the site of the lesion sometimes undesirable. As appropriate, they can be applied in combination with a bandage, particularly when it is desirable to increase penetration of the aminoguanidine composition into a lesion. Creams or oil-in-water emulsions and gels are absorbable and are the most cosmetically acceptable to the patient. (Guzzo et al, in *Goodman & Gilman's Pharmacological Basis of Therapeutics*, 9*th* Ed., p. 1593–15950 (1996)). Cream formulations generally include components such as petroleum, lanolin, polyethylene glycols, mineral oil, glycerin, isopropyl palmitate, glyceryl stearate, cetearyl alcohol, tocopheryl acetate, isopropyl myristate, lanolin alcohol, simethicone, carbomen, methylchlorisothiazolinone, methylisothiazolinone, cyclomethicone and hydroxypropyl methylcellulose, as well as mixtures thereof.

Other formulations for topical application include shampoos, soaps, shake lotions, and the like, particularly those formulated to leave a residue on the underlying skin, such as the scalp (Arndt et al, in *Dermatology In General Medicine* 2:2838 (1993)).

In general, the concentration of the aminoguanidine composition in the topical formulation is in an amount of about 0.5 to 50% by weight of the composition, preferably about 1 to 30%, more preferably about 2–20%, and most preferably about 5–10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective. The stratum corneum may act as a reservoir and allow gradual penetration of a drug into the viable skin layers over a prolonged period of time.

In a topical application, a sufficient amount of aminoguanidine must penetrate a patient's skin in order to obtain a desired pharmacological effect. It is generally understood that the absorption of drug into the skin is a function of the nature of the drug, the behavior of the vehicle, and the skin. Three major variables account for differences in the rate of absorption or flux of different topical drugs or the same drug in different vehicles; the concentration of drug in the vehicle, the partition coefficient of drug between the stratum corneum and the vehicle and the diffusion coefficient of drug in the stratum corneum. To be effective for treatment, a drug must cross the stratum corneum which is responsible for the barrier function of the skin. In general, a topical formulation which exerts a high in vitro skin penetration is effective in vivo. Ostrenga et al (*J. Pharm. Sci.*, 60:1175–1179 (1971) demonstrated that in vivo efficacy of topically applied steroids was proportional to the steroid penetration rate into dermatomed human skin in vitro.

A skin penetration enhancer which is dermatologically acceptable and compatible with aminoguanidine can be incorporated into the formulation to increase the penetration of aminoguanidine from the skin surface into epidemal keratinocytes. A skin enhancer which increases the absorption of aminoguanidine into the skin reduces the amount of aminoguanidine needed for an effective treatment and provides for a longer lasting effect of the aminoguanidine formulation. Skin penetration enhancers are well known in the art. For example, dimethyl sulfoxide (U.S. Pat. No. 3,711,602); oleic acid, 1,2-butanediol surfactant (Cooper, *J. Pharm. Sci.*, 73:1153–1156 (1984)); a combination of ethanol and oleic acid or oleyl alcohol (EP 267,617), 2-ethyl-1, 3-hexanediol (WO 87/03490); decyl methyl sulphoxide and Azone® (Hadgraft, *Eur. J. Drug. Metab. Pharmacokinet*, 21:165–173 (1996)); alcohols, sulphoxides, fatty acids, esters, Azone®, pyrrolidones, urea and polyoles (Kalbitz et al, *Pharmazie*, 51:619–637 (1996));

terpenes such as 1,8-cineole, menthone, limonene and nerolidol (Yamane, *J. Pharmacy & Pharmocology*, 47:978–989 (1995)); Azone® and Transcutol (Harrison et al, *Pharmaceutical Res.* 13:542–546 (1996)); and oleic acid, polyethylene glycol and propylene glycol (Singh et al, *Pharmazie*, 51:741–744 (1996)) are known to improve skin penetration of an active ingredient.

Levels of penetration of an aminoguanidine composition can be determined by techniques known to those of skill in the art. For example, radiolabeling of aminoguanidine, followed by measurement of the amount of radiolabeled aminoguanidine absorbed by the skin enables one of skill in the art to determine levels of the composition absorbed using any of several methods of determining skin penetration of the test compound. Publications relating to skin penetration studies include Reinfenrath, W G and G S Hawkins. *The Weanling Yorkshire Pig as an Animal Model for Measuring Percutaneous Penetration*. In:*Swine in Biomedical Research* (M. E. Tumbleson, Ed.) Plenum, New York, 1986, and Hawkins, G. S. *Methodology for the Execution of In Vitro Skin Penetration Determinations*. In: *Methods for Skin Absorption*, B W Kemppainen and W G Reifenrath, Eds., CRC Press, Boca Raton, 1990, pp.67–80; and W. G. Reifenrath, *Cosmetics & Toiletries*, 110:3–9 (1995).

For some applications, it is preferable to administer a long acting form of aminoguanidine composition using formulations known in the arts, such as polymers. Aminoguanidine can be incorporated into a dermal patch (Junginger, H. E., in Acta *Pharmaceutica Nordica* 4:117 (1992); Thacharodi et al, in *Biomaterials* 16:145–148 (1995); Niedner R., in *Hautarzt* 39:761–766 (1988)) or a bandage according to methods known in the arts, to increase the efficiency of delivery of the drug to the areas to be treated.

Optionally, the topical formulations of this invention can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

Aminoguanidine can be administered in an oral formulation in the form of tablets, capsules or solutions. An effective amount of the oral formulation is administered to patients 1 to 3 times daily until the symptoms of the proliferative disease are alleviated. The effective amount of aminoguanidine depends on the age, weight and condition of a patient. In general, the daily oral dose of aminoguanidine is less than 1200 mg, and more than 100 mg. The preferred daily oral dose is about 300–600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the aminoguanidine composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat skin proliferation disease.

Other therapeutic agents suitable for use herein are any compatible drugs that are effective for the intended purpose, or drugs that are complementary to the aminoguanidine formulation. As an example, the treatment with an formulation of this invention can be combined with other treatments such as a topical treatment with corticosteroids, calcipotrine, coal tar preparations, a systemic treatment with methotrexate, retinoids, cyclosporin A and photochemotherapy. The combined treatment is especially important for treatment of an acute or a severe skin proliferation disease. The aminoguanidine formulation utilized in a combination therapy may be administered simultaneously, or sequentially with other treatment, such that a combined effect is achieved.

Skin proliferation diseases which can be treated by using aminoguanidine composition include psoriasis, atopic dermatitis, non-specific dermatitis, primary irritant contact dermatitis, allergic contact dermatitis, lamellar ichthyosis, epidermolytic hyperkeratosis, pre-malignant sun induced keratosis, and seborrheic dermatitis in humans; and atopic dermatitis and mange in domesticated animals such as chronic hyperplastic dermatitis, fibropruritic nodules, acral lick dermatitis, actinic keratosis, and lichenoid keratosis in dogs and cats and similar diseases in other mammals.

The effect of treatment of a host with skin proliferation disease with an aminoguanidine composition can be evaluated by objective criteria such as an improvement of desquamation and erythema, reduction of the size of lesions as well as subjective criteria such as cessation of itching. Objective methods which are employed for establishing the effect of treatment of psoriasis patients include the resolution of plaques by visual monitoring and with photography. The visual scoring is done using PASI (Psoriasis Area and Severity Index) score (see Fredericksson, A J, Peterssonn B C *Dermatologies* 157:238–244 (1978)).

The following examples are presented as illustrations, not limitations.

EXAMPLES

Example 1

Psoriasis Case Study

A 44-year-old Caucasian male was diagnosed as having chronic plaque psoriasis. The initial manifestation was on his head (1968); the disease then progressed over the years to other parts of his body. In 1974, involvement of the elbows (bilateral), variable in size and severity, was seen. In 1990, involvement of the right knee after trauma, variable in size and severity, was seen also.

Status Before Treatment With Aminoguanidine

Head: almost 90% of head involved with severe desquamation, erythema and roughness of the skin to the touch. Patient reported severe itching.

Trunk: no signs of psoriasis.

Upper Extremities:

Right Elbow Region: 8×2 cm of area involved, lesions spotted, with the largest being 2×0.5 cm, total of 4 fields, moderate in duration, little erythema and desquamation, no itching reported;

Left Elbow Region: 7×1.5 cm, lesions spotted, with the biggest field being 1.5×1.5 cm, moderate in duration, little erthema and desquamation, no itching reported;

Lower Extremities: 6×5 cm of area involved with severe induration, erthema desquamation, and itching reported. PASI score 7.9.

History of Medication

The patient previously was treated with Stie-Lasan (containing 0.4% Dithranol and 0.4% salicylic acid) for 3 months in 1970, which had a major effect on desquamation, but increased itching and erythema. The patient reported increased itching. The therapy was impractical because of heavy squamation and discomfort. Thereafter, intermittent treatment was continued. No systemic medication was administered to this patient.

Formulation of Aminoguanidine 4 g aminoguanidine-hemisulfate was blended in a vehicle of 40 g Nivea® cream, a basic cream which contains mineral oil, glycerin, isopropyl palmitate, glyceryl stearate, cetearyl alcohol, tocopheryl acetate, isopropyl myristate, lanolin alcohol, simethicone, carbomen, methylchlorisothiazolinone, methylisothiazolinone,and hydroxypropyl methylcellulose (Nivea, Beiersdor, Inc., Norwalk, Conn.). The formulation was applied once daily for 2 weeks on only the lower extremity lesion.

Response to Treatment

The patient reported immediate cessation of itching, with no recurrence 6 weeks after ending treatment. Additionally, there was improvement of desquamation after 3 days. Improvement of erythema after 7 days also was noted. Even after cessation of aminoguanidine therapy, a prolonged effect lasted for at least 6 weeks with only minor recurrence of itching, mild erythema and still without squameous formations.

Example 2

Psoriasis Treatment Result

Figure 1B:
Figure 2A:
FIGS. 2A and 2B are images of a patient inflicted with a psoriasis lesion on one side of his head treated with vehicle alone (FIG. 2A) and then with aminoguanidine in the vehicle (FIG. 2B).
Figure 2B:
Figure 3A:
FIGS. 3A and 3B are images of a patient inflicted with psoriasis on his right knee treated with vehicle alone (FIG. 3A) and then with aminoguanidine in the vehicle (FIG. 3B).
Figure 3B:

The same patient as in Example 1 was topically treated with vehicle (Nivea® creme) once daily for 4 days on the lesions on the head and on the right knee. As shown in FIGS. 1A, 2A and 3A, there was no reduction in psoriatic symptoms or lesions after treatment with vehicle alone; prominent silver scaly lesions and raised plaques remained. The patient was then treated with a 10% (w/w) formulation including vehicle and the aminoguanidine prepared according to Example 1. After 4 days of treatment, the scaly lesions and the raised plaques went away (see FIGS. 1B, 2B and 3B), and the patient reported that the itching stopped.

Example 3

Clinical Study

The purpose of this study is to compare the treatment with 10% (w/w) aminoguanidine of psoriatic plaques on one side of the body with a treatment with vehicle alone of a plaque on the contralateral side of the body.

Study Population

10–20 adult male/female patients of 18 years of age or older with chronic, plaque type psoriasis, who are not currently on any systemic treatment for psoriasis are selected for the study. The following patients are excluded from the study:

Patients taking or using systemic anti-inflammatory medication (e.g. corticosteroids), or who have taken or used them in the previous four weeks.

Patients using or who have used systemic antipsortiasis treatment (e.g. methotrexate) within the previous four weeks.

Patients using immunosuppressive drugs.

Patients using OTC/Rx topical drugs to the areas to be treated (test sites) during the past 1 week. Patients are allowed to use topical prescription drugs on areas of the body other than the selected test sites.

Patients who are known to be HIV positive.

Pregnancy.

Test Materials

Placebo: Nivea® creme alone

Active Cream: Nivea® creme containing 10% (w/w) aminoguanidine.

The patients selected for the study are instructed to apply active cream 1–3 times a day to plaques on one side of the body and, if possible, base cream to a plaque on the contralateral side of the body. The applications are performed mornings, afternoons and evenings for a period of 4 weeks. The creams are labeled A and B. Neither the panelist nor the principal investigator knows the exact nature of the creams applied. The areas of the body of different patients receiving either cream A or B are selected by random rotation. Twice a week, the patients return to the laboratory for a determalogical examination and possible photographs of the treatment sites. In addition, photographs are taken at the first and last visits. The patients are asked to maintain a diary to evaluate both estetic qualities of the cream and subjective symptoms (i.e., itching, stinging, burning, amount scales).

Evaluation

Resolution of the plaque(s) is monitored visually and with photography. The visual scoring is done using a modified Psoriasis Area and Severity Index (PASI) score. The individual with psoriasis is seen in the laboratory twice a week. The patients are scored at a minimum on Day 1 (baseline), at the end of week two (Day 14) and week four (Day 28). If dramatic improvement occurs earlier than Day 14, the patients are scored and photographed earlier.

The above examples demonstrate methods of preparing a topical formulation of aminoguanidine. The examples also demonstrate that treatment of psoriasis with an aminoguanidine formulation (10% w/w) alleviates psoriatic symptoms.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for treating psoriasis, sand method comprising:

contacting a psoriatic lesion with an aminoguanidine composition containing between 1–30 weight percent aminoguanidine in a carrier for topical application, in an amount sufficient to alleviate at least one symptom selected from the group consisting of reducing size, thickness or scales of a psoriatic lesion, reducing erythema, decreasing itching and decreasing induration.

2. The method according to claim 1, wherein said composition is a cream, an ointment, a lotion, a gel, or a patch.

3. A composition comprising:

aminoguanidine in a concentration about 1–30% by weight of said composition, effective to alleviate at least one symptom of a skin disease caused by or associated with hyperproliferation of keratinocytes, when administered to a mammal suffering from said skin disease, wherein said composition (i) does not include an active thiol agent, and (ii) is in the form of a stick, an oil, an ointment, a cream, a gel, a lotion, a paste, or a patch.

4. The composition according to claim 3, wherein said aminoguanidine concentration is about 2–20% by weight of said composition.

5. The composition according to claim 3, said composition further comprising a skin penetration enhancer.

6. The pharmaceutical composition according to claim 5, wherein said carrier is an oil-in-water emulsion.

* * * * *